(12) United States Patent
Francischelli et al.

(10) Patent No.: US 8,801,707 B2
(45) Date of Patent: Aug. 12, 2014

(54) METHOD AND DEVICES FOR TREATING ATRIAL FIBRILLATION BY MASS ABLATION

(75) Inventors: David E. Francischelli, Brooklyn Park, MN (US); Mark T. Stewart, Brooklyn Park, MN (US); James R. Skarda, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 32 days.

(21) Appl. No.: 13/584,932

(22) Filed: Aug. 14, 2012

(65) Prior Publication Data

US 2012/0316488 A1    Dec. 13, 2012

Related U.S. Application Data

(62) Division of application No. 11/128,786, filed on May 13, 2005, now abandoned.

(60) Provisional application No. 60/571,182, filed on May 14, 2004.

(51) Int. Cl.
| | |
|---|---|
| *A61B 18/14* | (2006.01) |
| *A61N 7/02* | (2006.01) |
| *A61B 18/00* | (2006.01) |
| *A61B 17/22* | (2006.01) |

(52) U.S. Cl.
CPC ....... *A61N 7/022* (2013.01); *A61B 2018/00839* (2013.01); *A61B 2018/00363* (2013.01); *A61B 2018/00291* (2013.01); *A61B 17/2202* (2013.01); *A61B 2018/00351* (2013.01); *A61B 2018/1472* (2013.01); *A61B 2018/00577* (2013.01); *A61B 2018/00357* (2013.01); *A61B 2018/00267* (2013.01); *A61B 18/1492* (2013.01)
USPC .......................................... 606/41

(58) Field of Classification Search
USPC ..................... 606/27, 41, 45, 49, 50; 600/439
See application file for complete search history.

(56) References Cited

U.S. PATENT DOCUMENTS

| | | | |
|---|---|---|---|
| 3,736,936 A | 6/1973 | Basiulis et al. | |
| 3,807,403 A | 4/1974 | Stumpf et al. | |

(Continued)

FOREIGN PATENT DOCUMENTS

| | | |
|---|---|---|
| EP | 0916360 | 5/1999 |
| EP | 1095627 | 5/2001 |

(Continued)

OTHER PUBLICATIONS

Reexam Cert 4794F or 5,697,536, Jun. 10, 2003, Eggers et al.

(Continued)

*Primary Examiner* — Michael Peffley
*Assistant Examiner* — Khadijeh Vahdat

(57) ABSTRACT

Apparatus and method for ablating target tissue including a non-linear area of tissue in the left atrium of a patient. The method can include selecting an ablation apparatus having an ablator with a tissue engagement section, penetrating a chest cavity of the patient, and identifying the target tissue. The method can also include positioning the ablation apparatus adjacent to the target tissue so that the tissue engagement section can transfer ablation energy to the target tissue. The method can further include energizing the tissue engagement section with ablation energy in order to create a footprint on the non-linear area of tissue in the left atrium and to reduce an overall mass of excitable tissue in the left atrium.

10 Claims, 10 Drawing Sheets

(56) References Cited

U.S. PATENT DOCUMENTS

| | | |
|---|---|---|
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,562,900 A | 1/1986 | Anderson et al. |
| 4,598,698 A | 7/1986 | Siegmund |
| 4,601,290 A | 7/1986 | Effron et al. |
| 4,664,110 A | 5/1987 | Schanzlin |
| 4,671,274 A | 6/1987 | Sorochenko |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,147,355 A | 9/1992 | Freidman et al. |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,334,181 A | 8/1994 | Rubinsky et al. |
| 5,334,193 A | 8/1994 | Nardella |
| 5,341,466 A | 8/1994 | Perlin et al. |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,402,792 A | 4/1995 | Kimura |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,413,550 A | 5/1995 | Castel |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,499 A | 8/1995 | Fritzsch |
| 5,443,463 A | 8/1995 | Stern et al. |
| 5,443,470 A | 8/1995 | Stern et al. |
| 5,448,994 A | 9/1995 | Iinuma |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Sliwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |

(56) References Cited

U.S. PATENT DOCUMENTS

| | | |
|---|---|---|
| 5,681,278 A | 10/1997 | Igo et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Lanard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,735,290 A | 4/1998 | Sterman et al. |
| 5,755,760 A | 5/1998 | Maguire et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,960 A | 8/1998 | Stevens et al. |
| 5,800,428 A | 9/1998 | Nelson et al. |
| 5,800,482 A | 9/1998 | Pomeranz et al. |
| 5,810,802 A | 9/1998 | Panescu et al. |
| 5,817,021 A | 10/1998 | Reichenberger |
| 5,827,216 A | 10/1998 | Igo et al. |
| 5,836,947 A | 11/1998 | Fleischman et al. |
| 5,840,030 A | 11/1998 | Ferek-Petric et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,871,523 A | 2/1999 | Fleischman et al. |
| 5,871,525 A | 2/1999 | Edwards et al. |
| 5,873,845 A | 2/1999 | Cline et al. |
| 5,876,399 A | 3/1999 | Chia et al. |
| 5,879,295 A | 3/1999 | Li et al. |
| 5,879,296 A | 3/1999 | Ockuly et al. |
| 5,881,732 A | 3/1999 | Sung et al. |
| 5,882,346 A | 3/1999 | Pomeranz et al. |
| 5,885,278 A | 3/1999 | Fleischman |
| 5,893,848 A | 4/1999 | Negus et al. |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,954,661 A | 9/1999 | Greenspon et al. |
| 5,971,980 A | 10/1999 | Sherman |
| 5,971,983 A | 10/1999 | Lesh |
| 5,993,447 A | 11/1999 | Blewett et al. |
| 6,004,269 A * | 12/1999 | Crowley et al. ............... 600/439 |
| 6,007,499 A | 12/1999 | Martin et al. |
| 6,012,457 A | 1/2000 | Lesh |
| 6,016,811 A | 1/2000 | Knopp et al. |
| 6,042,556 A | 3/2000 | Beach et al. |
| 6,056,745 A | 5/2000 | Panecsu et al. |
| 6,063,081 A | 5/2000 | Mulier |
| 6,071,279 A | 6/2000 | Whayne et al. |
| 6,088,894 A | 7/2000 | Oakley |
| 6,090,084 A | 7/2000 | Hassett et al. |
| 6,096,037 A | 8/2000 | Mulier |
| 6,113,592 A | 9/2000 | Taylor |
| 6,117,101 A | 9/2000 | Diederich et al. |
| 6,120,496 A | 9/2000 | Whayne et al. |
| 6,142,993 A | 11/2000 | Whayne et al. |
| 6,142,994 A | 11/2000 | Swanson et al. |
| 6,152,920 A | 11/2000 | Thompson et al. |
| 6,161,543 A | 12/2000 | Cox et al. |
| 6,165,174 A | 12/2000 | Jacobs et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,296,619 B1 | 10/2001 | Brisken et al. |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,488,680 B1 | 12/2002 | Francischelli |
| 6,502,575 B1 | 1/2003 | Jacobs et al. |
| 6,514,250 B1 | 2/2003 | Jahns |
| 6,527,767 B2 | 3/2003 | Wang et al. |
| 6,537,248 B2 | 3/2003 | Mulier |
| 6,537,272 B2 | 3/2003 | Christopherson et al. |
| 6,558,382 B2 | 5/2003 | Jahns |
| 6,575,956 B1 | 6/2003 | Brisken et al. |
| 6,584,360 B2 | 6/2003 | Francischelli |

(56) References Cited

U.S. PATENT DOCUMENTS

| | | |
|---|---|---|
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,626,855 B1 | 9/2003 | Weng et al. |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,918,908 B2 | 7/2005 | Bonner et al. |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 7,438,714 B2 | 10/2008 | Phan |
| 2002/0002372 A1 | 1/2002 | Jahns et al. |
| 2003/0045872 A1 | 3/2003 | Jacobs |
| 2003/0144656 A1 | 7/2003 | Ocel |
| 2003/0191462 A1 | 10/2003 | Jacobs |
| 2003/0199867 A1 | 10/2003 | Wellman |
| 2003/0216724 A1 | 11/2003 | Jahns |
| 2004/0015106 A1 | 1/2004 | Coleman |
| 2004/0015219 A1 | 1/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0059962 A1* | 3/2005 | Phan et al. ............... 606/41 |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |

FOREIGN PATENT DOCUMENTS

| | | |
|---|---|---|
| WO | WO97/25917 | 7/1997 |
| WO | WO99/44524 | 9/1999 |
| WO | WO01/80755 | 11/2001 |

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Techique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," J of Thorac Cardiovasc Surg, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

(56) References Cited

OTHER PUBLICATIONS

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8 1/2 Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

\* cited by examiner

METHOD AND DEVICES FOR TREATING ATRIAL FIBRILLATION BY MASS ABLATION

RELATED APPLICATIONS

This application is a Division of and claims the benefit of Ser. No. 11/128,786, filed May 13, 2005, which claims the benefit of the filing date of U.S. Provisional Patent Application No. 60/571,182 filed on May 14, 2004, which is incorporated herein by reference in its entirety.

FIELD OF THE INVENTION

The present invention relates to tools and procedures generally and relates more particularly to the use of ablation to reduce the mass of excitable tissue of the left atrium to prevent and treat atrial fibrillation or other medical conditions.

BACKGROUND

Focal triggers initiating atrial fibrillation are thought to frequently arise from the pulmonary veins and their ostia. Surgeons have used the technique of modifying the substrate of the heart in these areas to prevent the propagation of the arrhythmia. In some patients with chronic atrial fibrillation, the Cos/MAZE III procedure has been employed. This procedure controls propagation of the depolarization wavefronts in the right and left atria by means of surgical incisions through the walls of the right and left atria. The incisions create blind or dead end conduction pathways, which prevent re-entrant atrial tachycardias from occurring.

While the Cox/MAZE procedure is successful is treating atrial fibrillation, the procedure is quite complex and is currently practiced by only a few very skilled cardiac surgeons in conjunction with other open-heart procedures. The procedure also is quite traumatic to the heart, as in essence, the right and left atria are cut into pieces and sewed back together, to define lines of lesion across which the depolarization wavefronts will not propagate. Still today, the Cox/MAZE procedure is done with traditional cut and sew techniques.

The market is demanding quicker, safer and less invasive approaches. As a result, there has been much recent research sod evaluation of mechanisms to encircle and isolate the pulmonary veins and replicate fee incisions of the MAZE operation. Companies are developing ablation techniques that heat (or cool) or chemically destroy the underlying tissue along these lines.

It has been suggested that procedures similar to the MAZE procedure could be instead, performed by means, of electrosurgical ablation, for example, by applying radio frequency energy to internal or external surfaces of the atria to create lesions across which the depolarization wavefronts will not propagate. Such procedures are disclosed in U.S. Pat. No 5,895,417, issued to Pomeranz, et ah ("the Pomeranz '417 patent"); U.S. Pat. No, 5,575,764 issued to Swartz., et al. ("the Swartz '766 patent"); U.S. Pat. No, 6,032,077, issued to Pomeranz ("the Pomeranz '077 patent"); U.S. Pat. No. 6,142, 994, issued to Swanson, et at. ("the Swanson '994 patent"); and U.S. Pat. No. 5,871,523, issued to Fleischman, et al. ("the Fleischman '523 patent"), all incorporated herein by reference in their entireties.

The Pomeranz '417 patent discloses an apparatus for ablating tissue by making linear lesions within the chamber of a patient's heart by application of a plurality of spaced electrodes along an elongate member. The Schwartz '766 patent discloses a process for seating atrial arrhythmia, by creating discrete ablation tracks within both the left and right atrium. The Pomeranz '077 patent discloses an ablation catheter that is electrically connected to tissue to be ablated by a foam on the electrodes that is soaked in saline. The foam in the Pomeranz '077 patent acts as a conductive fluid to allow energy from the electrode to ablate the contacted tissue. The Swanson '994 patent discloses a surgical method and apparatus for positioning an element in the body of a patient for diagnosis or therapy. The apparatus in the Swanson '994 patent may be a catheter or a probe having a shaft with a lumen extending there through. The Fleischman '523 patent discloses a helically-wound emitter on an element with a insulating sheath movable over the emitter.

Various types of electrophyslology devices are used for ablating tissue. Typically, such devices include a conductive tip or blade that serves as one electrode In an electrical circuit that is completed via a grounding electrode coupled to the patient. The contact point is small or linear to create lesions to form linear tracks of ablated tissue. A power source creates high levels of electrical energy between the two electrodes causing the tissue to heat to a sufficient level to denature proteins within the tissue and cause cell death. In order for such procedures to be effective, if is desirable that the electrosurgically-created lesions are continuous along their length and extend completely through the tissue of the heart Manufacturers have developed catheters that have a linear army of electrodes along a long axis (e.g., the Amazr, MECCA, and Revelation catheters). The surgeon positions the catheter and electrodes in contact with the tissue and either individually or sequentially applies energy to each electrode. Additionally, catheters that incorporate an electrode that is energized and moves along its length have been proposed, such as the Flex-10 from AFx. Inc., of 47929 Fremont Ave. Fremont, Calif. 94538.

Surgeons have also bees able to create linear lesions on the heart using applications of the same techniques. For example, Kottkamp, et. al. in an article entitled "Intraoperative Radio Frequency Ablation of Chronic Atrial Fibrillation: A Left Atrial Curative Approach by Elimination of Anatomic 'Anchor' Reentrant Circuits," *Journal of Cardiovascular Electrophysiology,* 10:772-780 (1999), describe a hand-held device that creates as series of spot or short (less than 1 cm) linear lesions. Other investigators have used long, linear unipolar probes to create somewhat longer lesions. Still others have used multi-electrode linear catheters, similar to those described above to create a series of ablations that net a linear lesion.

The focus of most investigators has been to isolate the pulmonary veins. There is growing research that suggests this may not he necessary in the prevention and cure of atrial fibrillation, as discussed in the article by G. Stabile, P. Turco, V. La Rocca, F. Nocerino, E. Stabile, and A. De Simone entitled "Is Pulmonary Vein Isolation Necessary for Curing Atrial Fibrillation?," *Circulation,* 108:657-660 (2003). Rather than focusing on only isolating the pulmonary veins, reduction in the overall volume of excitable tissue in the left atrium is sufficient to prevent atrial, fibrillation. The general concept is to ablate a large enough nonlinear area of the left atrium to prevent re-entrant waves and the propagation of atrial fibrillation.

SUMMARY OF THE INVENTION

Some embodiments of the invention provide a method of ablating target tissue including a non-linear area of tissue in the left atrium of a patient. The method can include selecting an ablation apparatus having an ablator or ablation member with a tissue engagement section, penetrating a chest cavity of the patient, and identifying the target tissue. The method can also include positioning the ablation apparatus adjacent to the target tissue so that the tissue engagement section can transfer ablation energy to the target tissue. The method can further include energizing the tissue engagement section with ablation energy in order to create a footprint on the non-linear area of tissue in the left atrium and to reduce an overall mass of excitable tissue in the left atrium.

In some embodiments, an ablation apparatus can include an insertion tool having a proximal end, a distal end, and a lumen. The ablation apparatus can include an ablator or ablation member having a conductor and a tissue engagement portion. The conductor can include a source end extending from the proximal end of the insertion tool and a delivery end coupled to the tissue engagement portion. The ablator can be removably inserted in the lumen. The ablation apparatus can also include ah energy source connected to the conductor. The insertion tool can be Inserted into a patient so that the distal end is adjacent the target tissue. The conductor can urge the ablator out of the lumen to engage the target tissue. Energy can be conducted from the energy source to the ablator to create a footprint on the target tissue to reduce an overall mass of excitable tissue.

DETAILED DESCRIPTION

Figure 1:
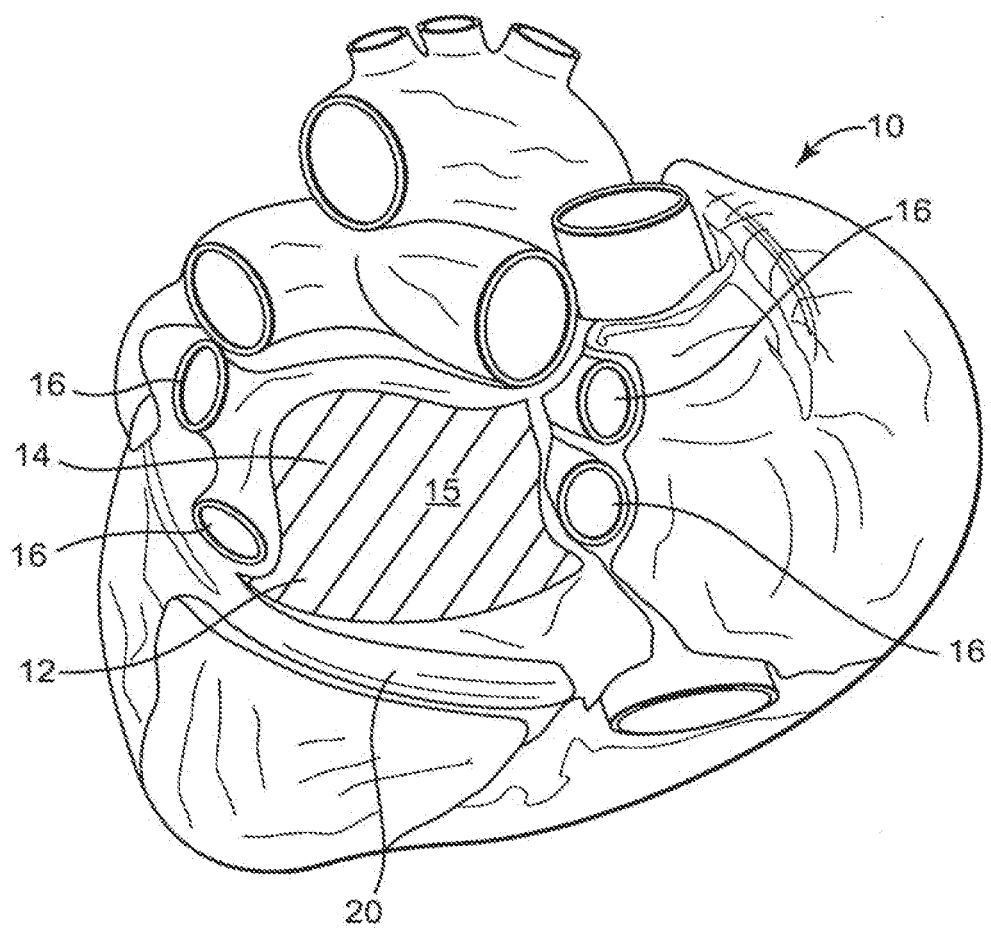
FIG. 1 is an illustration of a posteroinferior view of the human heart removed from the chest cavity.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

Some embodiments of the invention provide a method and apparatus for reducing the mass of the viable tissue (e.g., by rendering the mass of tissue non-contractile, non-viable, or unable to propagate an action potential) in the left atrium of the heart to prevent or cure atrial fibrillation. Some embodiments of the invention can include preventing reentry of depolarizing wavefront signals by ablating a large area of the left atrium. Furthermore, some embodiments of the invention can substantially prevent the sustenance of atrial fibrillation.

Embodiments of the invention can provide an ablation apparatus used to conduct ablating energy to a locale of contacted or non-contacted and possibly surrounding tissue with the intent to ablate an entire area, while not harming neighboring tissue. The ablation apparatus can include an electrode having a footprint of a dimension designed to cover a predetermined region of tissue in the left atrium.

According to some embodiments of the invention, an ablation apparatus can be used to ablate a non-linear area of the tissue in the left atrium en masse. This method can be performed by endocardial positioning of an ablation device in the left atrium either via a trans-atrial septal puncture or retrograde through the arterial system. Alternatively, embodiments of the invention can provide a method of ablating tissue In the left atrium in a predefined area by inserting an ablating apparatus using an epicardial approach with access to the posterior left atrium through the pericardial space, either by a sub-xiphoid or inter-costal incision.

Some embodiments of the invention provide a method of ablating tissue using a large footprint ablation electrode for the control, prevention, and cure of atrial fibrillation. The method can include ablating a predefined area of tissue in the left atrium, while protecting other areas of the heart, lungs, and esophagus using directional energy delivery, insulation, or standoffs to space, the ablation apparatus from protected areas. The method of ablating the heart tissue can include using a trans-venous catheter from the inside of the heart to deliver the ablation apparatus. Location and imaging techniques such as echogram, sonogram, magnetic resonance imaging, ultrasound, X-ray, sensors or transmitters on the ablation device, or other mapping technology can allow for proper placement to minimize damage to surrounding tissue.

Some embodiments of the invention include a locatable ablation apparatus having a predefined footprint that can be delivered through an incision in the chest wall in order to ablate by trans-myocardial engagement with a bipolar electrode. The ablation apparatus cars use any of suitable method and/or procedure with electro-surgical devices or other types of ablation devices (e.g., thermal ablation, micro-wave ablation, cryogenic ablation, ultrasound ablation, etc.) to ablate tissue in the left atrium to reduce the mass of excitable tissue therein.

The apparatuses and methods of some embodiments of the invention are designed to reduce the overall excitable mass of the left atrium and to reduce or cure atrial fibrillation (AF). Some embodiments of the invention use radio frequency energy to create heat and ablate an area of tissue. However, other embodiments of the invention may include additional or alternative energy sources, such as microwave, cryogenic, ultrasound, laser, thermal, etc. Also, some embodiments of the invention can be used for creating ablation lesions in other areas of the heart, such as the ventricles.

FIG. 1 illustrates the human heart 10 from a posteroinferior view. The left atrium 12 includes an external surface 14 of an area target tissue 15, which includes the area of tissue to be ablated. In some embodiments, the target tissue 15 can be defined as the entire left atrial posterior wall tissue extending around, but not including, the pulmonary veins. As shown in FIG. 1, the target tissue 15 can be generally spaced from the pulmonary veins 16 to prevent damage to the pulmonary veins 16. Coronary sinus 20 is also identified.

Figure 2:
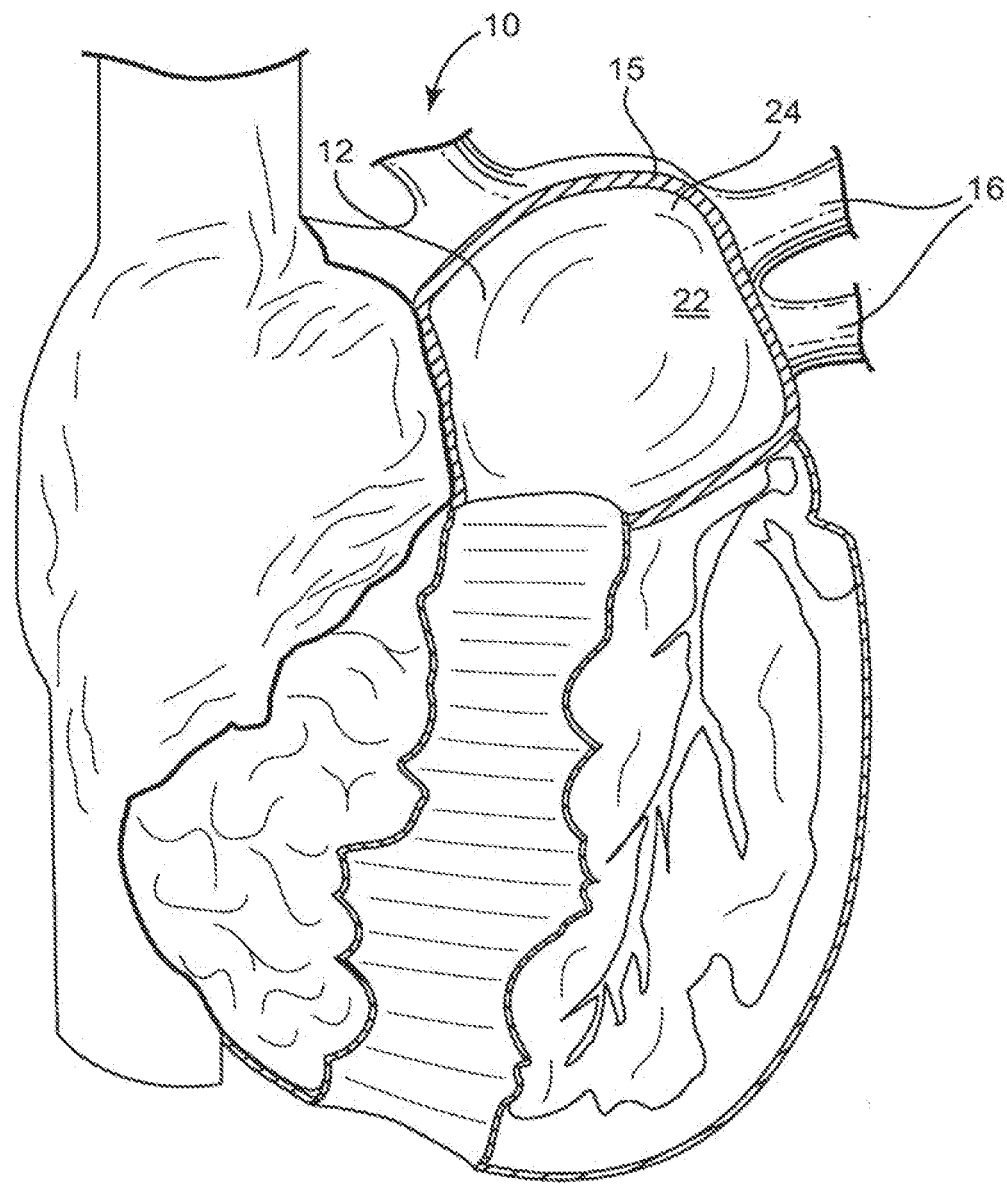
FIG. 2 is an illustration of a cross-section of the human heart showing the left atrium and the ostia leading to the pulmonary veins.

As shown in FIG. 2, an inner chamber 22 of the left atrium 12 includes an internal surface 24 of the target tissue 15. The pulmonary veins 16 themselves are generally not included in the target tissue 13 due to concern over vein stenosis. The internal surface 24 of the target tissue 15 may be defined as the entire left atrial posterior wall tissue extending into the ostial regions surrounding the pulmonary veins 16, but not extending over into the lumen of the pulmonary veins, extending to near the mitral valve annulus. There is interest in creating conduction block in the area between one or both of the right inferior pulmonary vein and the mitral valve annulus. Tissue to be protected can include all tissue in the patient not defined as the target tissue 15. Tissue to be protected can be isolated to prevent damage. The target tissue 15 can be spaced from the ostia of the pulmonary veins 16, but may extend to areas surrounding the pulmonary vein ostia as well.

Figure 3:
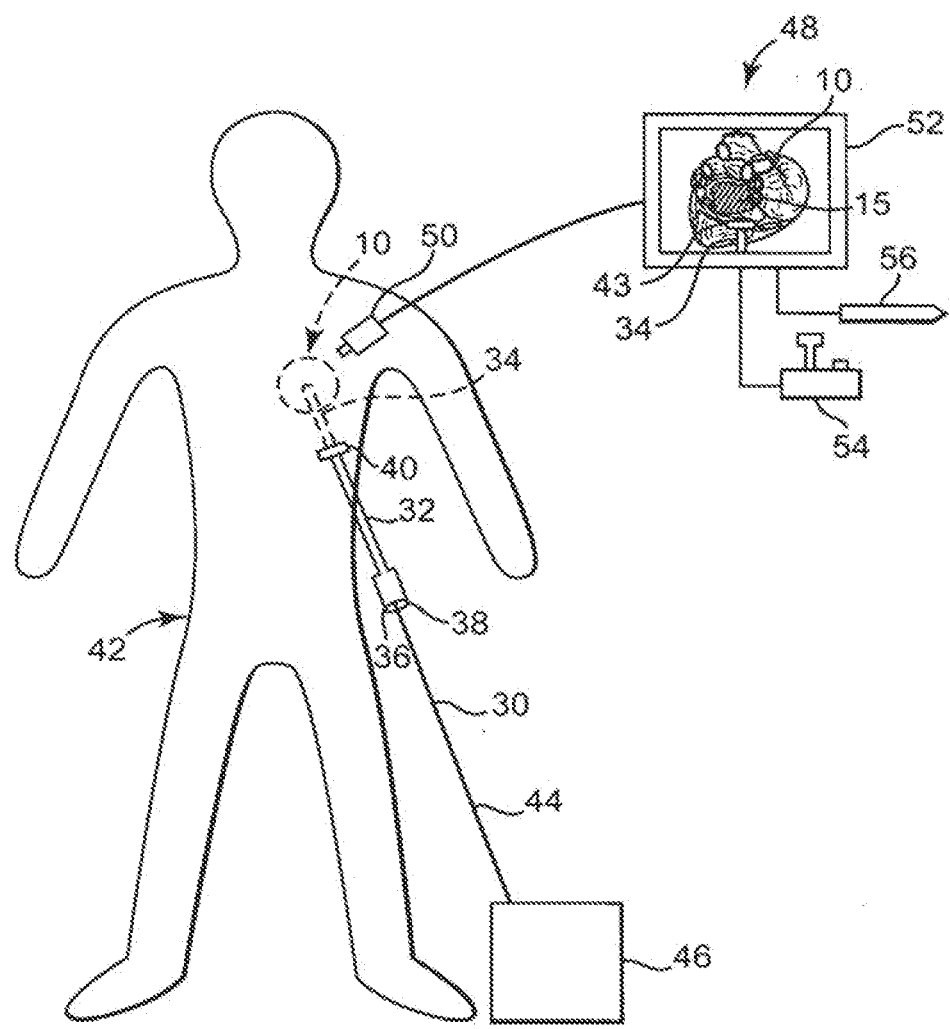
FIG. 3 is a schematic illustration of an ablation apparatus according to one embodiment of the invention shown being applied to a patient.

FIG. 3 illustrates an ablation apparatus 30 according to one embodiment of the invention for ablating the target tissue 15. The ablation apparatus 30 can include or be used in conjunction with an insertion tool 32, such as a trocar, an endoscopy port, a catheter, etc. The insertion tool 32 can include a distal end 34 and a proximal end 36. The ablation apparatus 30 can also include a lumen 38 that can extend through the insertion tool 32 and can open at the distal end 34 and/or the proximal end 36 of the insertion tool 32. The ablation apparatus 30 can further include an ablator 43 that can extend from the distal end 34 of the insertion tool 32. The ablator 43 can be inserted in the lumen 38 for delivery through an Incision 40 In the patient 42. A conductor 44 can extend through the lumen 38 to connect the ablator 43 to a power source 46. The power source 46 can be a source of ablation energy, such as radio frequency energy. Other forms of ablative methods and energy sources can be used with the ablator 43. Other forms of ablation techniques include, but are not limited to, microwave, ultrasound, heat, cryogenic, radiation, and chemical ablation.

Proper positioning of the ablator 43 on the targeted tissue 15 can be performed by any suitable means, such as direct visualization, fluoroscopic X-ray visualization, ultrasound positron emission tomography, fluoroscopy, intra-cardiac echo, transesophageal echo, magnetic resonance imaging, computerized tomography, or by endoscopic imaging. As shown in FIG. 3, a mapping tool 48 can include a sensor 50 connected to a display 32 to represent or visualize the position of the ablator 43 with respect to the target tissue 15. An input device, such as a toggle stick 54 or a pointer pen 56, can be used to identify the target tissue 15 on the heart 10.

Figure 4B:
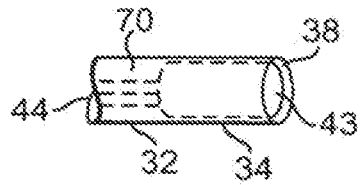
FIG. 4B is a partial perspective view of a distal end of an insertion tool having the ablator of FIG. 4 removably inserted therein.
Figure 4:
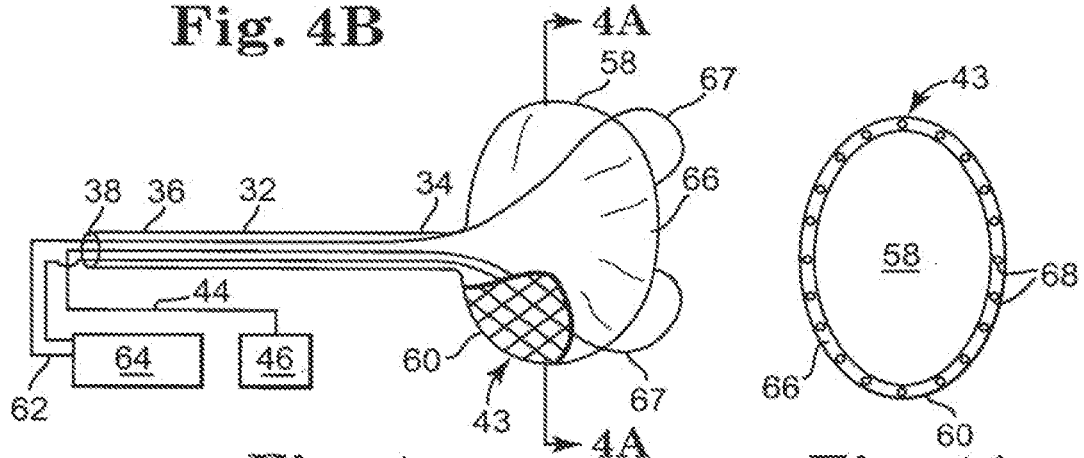
FIG. 4 is a top view of an ablation apparatus according to another embodiment of the invention with an ablator on an insulated balloon.
Figure 4A:
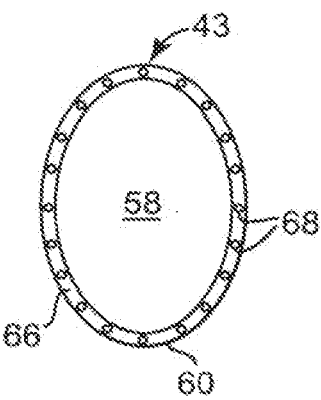
FIG. 4A is a cross-sectional view along the line 4A-4A of FIG. 4.
Figure 5:
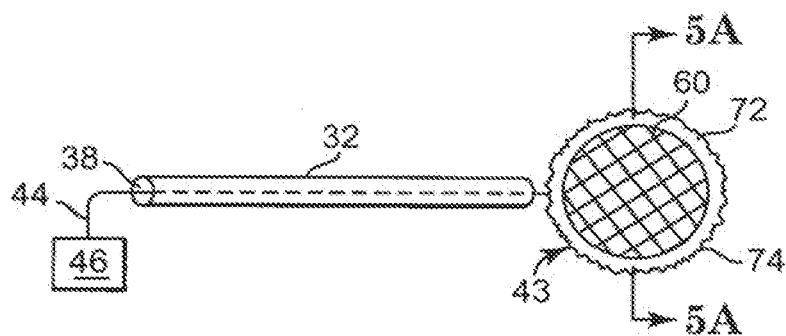
FIG. 5 is a top view of an ablation apparatus according to another embodiment of the invention with an ablator as a patch.
Figure 6:
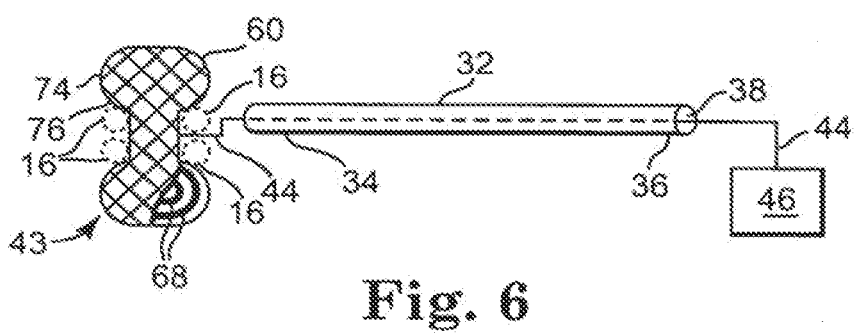
FIG. 6 is a top view of an ablation apparatus according to another embodiment of the invention with an ablator as a contoured patch.

The ablator 43 can include a tissue engagement section 60 (as shown in FIGS. 4-6), which can include a footprint that allows the tissue engagement section 60 to ablate a predefined area with each energization.

As shown in FIG. 4, the ablator 43 can include a balloon 58 having a tissue engagement section 60 with a footprint for endocardial or epicardial application. The footprint can be of a size and shape to conform to the individual patient requirements. The balloon 58 may include an inflate tube 62 positioned in the insertion tool 32. The inflator tube 62 can be connected to an inflation source 64 for inflating the balloon 58 with air, $CO^2$, saline, etc. An insulator 66 on the balloon 58 can protect adjacent tissue from the energy in the ablator 43, while ablating the target tissue 15 bearing against the footprint of the tissue engagement section 60. Additional insulation can be achieved by the saline or gas in the balloon 58. The insertion tool 32 can be flexible or rigid to help the surgeon manipulate the position of the balloon 58 to bring the tissue engagement section 60 in contact with the target tissue 15. The inflation source 64 can direct liquid or gas through the inflator tube 62 to inflate the balloon 58. The balloon 58 can expand to cause the tissue engagement section 60 to bear against the target tissue 15. In some embodiments, as shown in FIG. 4, bowing struts 67 can be deployed within the left atrium 12 to push the ablator 43 Into contact with the left atrial posterior wall. When deployed in the pericardial space, the balloon 58 may be inflated to force contact of the tissue engagement section 60 with the epicardial target tissue 15.

In some embodiments, the balloon 58 can include a conducting surface that acts as a tissue engagement section 60. A collapsed balloon 58 can be inserted into the left atrium 12 or into the pericardial space surrounding the epicardial surface of the target tissue 15. In one embodiment, the balloon 58 can then be inflated with saline from the inflation source 64 and oriented such that a thermally-transmissive, tissue engagement section 60 of the balloon 58 can be positioned against the posterior left atrium and an insulated portion of the balloon 58 can be positioned against the anterior left atrium. The saline can be heated by electrical current supplied by power source 46 to a temperature between 50 degrees Celsius and 85 degrees Celsius, and in some embodiments, between 55 degrees Celsius and 65 degrees Celsius. At these temperatures, the cells in the target area 15 generally die without collages shrinkage. Alternatively, the balloon 58 can be cooled with cryogenic technology to freeze the atrial tissue and ablate the target tissue 15. Generally, temperatures for cryogenic therapy must he less than negative 20 degrees Celsius to negative 40 degrees Celsius.

FIG. 4 illustrates a cross section of the balloon 58 with the insulator 66 surrounding the ablator 43. The ablator 43 can include one or more ablating elements 68 on the tissue engagement section 60 for transferring the energy of the power source 46 to the target tissue 15. Ablating elements 68 may comprise one or more electrodes, ultrasound, transducers, microwave antennae, cryogenic elements, chemical elements and/or radioactive elements, for example. Insertion of the balloon 58 into the left atrium 12 allows the balloon 58 to be manipulated during inflation to bring the ablating elements 68 of the tissue engagement section 60 to bear against the target tissue 15 and to space the ablating elements 68 from the tissue to be protected. The insulator 66 can protect adjacent tissue not within the area of the target tissue 15.

The ablator 43 can be delivered to the desired location in the patient using the insertion tool 32, such as a catheter 70, as shown in FIG. 4B. The footprint of the ablator 43 can be configured for any patient anatomy and/or any ablation pattern desired. The collapsed balloon 58 of the ablator 43 can be removably inserted through the distal end 34 of the catheter 70, so that the conductor 44 extends through the insertion tool 32, as shown in FIG. 4B, the catheter 70 can be inserted into the patient 42 (as described with respect to FIG. 3) to position the distal end 34 adjacent the target tissue 15. The conductor 44 can be used to push the ablator 43 out of the lumen 38 to a position extending from the distal end 34, as shown in FIG. 4.

Figure 5A:
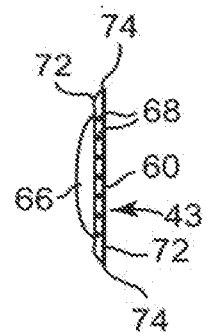
FIG. 5A is a cross-sectional view of the ablation apparatus along line 5A-5A of FIG. 5.

FIGS. 5 and 5A illustrate an embodiment of a circular ablator 43. In other embodiments, the ablator 43 can be elliptical, oval, etc. The circular ablator 43 can include a tissue engagement surface 60 and an outside skirt 72. The outside skirt 72 can be used as a stand-off to space the tissue engagement surface 60 from delicate tissue, such as the pulmonary veins 16. The circular ablator 43 can include one or more ablating elements 68 on the tissue engagement surface 60 and an insulation layer 66 on the opposite surface, as shown in FIG. 5A. The ablating elements 68 can be positioned in a helical or circular pattern. The outside skirt 72 can be constructed of a soft, heat-insulating material, such as silicone or other elastomeric material. The outside skirt 72 can include an outer edge 74 constructed of a resilient material to positively space the ablating elements 68 from the tissue to be protected.

The circular ablator 43 can be used epicardially by insertion within the pericardial space adjacent the posterior left atrium. In one embodiment, the circular ablator 43 can alternatively include an uncoiling spiral configuration. The uncoiling spiral can he positioned through a sheath 32, and when advanced beyond the sheath 32, can uncoil to take the desired shape. Pre-formed shape memory or superelastic alloys, such as NiTi, can be used to ensure that the spiral uncoils into the desired shape.

In another embodiment, two circular ablators 43 can he used in a bipolar arrangement. One ablator 43 can be on the external surface 14 of the target tissue 15 and another ablator 43 can be positioned on the internal surface 24 of the target tissue 15 in the left atrium 12. The bipolar circular ablator 43 can also be positioned using an uncoiling spiral configuration. The uncoiling spiral can be positioned through a sheath 32, and when advanced, beyond the sheath 32, can uncoil to take the desired shape. Pre-formed shape memory or superelastic alloys, such as NiTi, can be used to ensure that the spiral uncoils into the desired shape.

Figure 15:
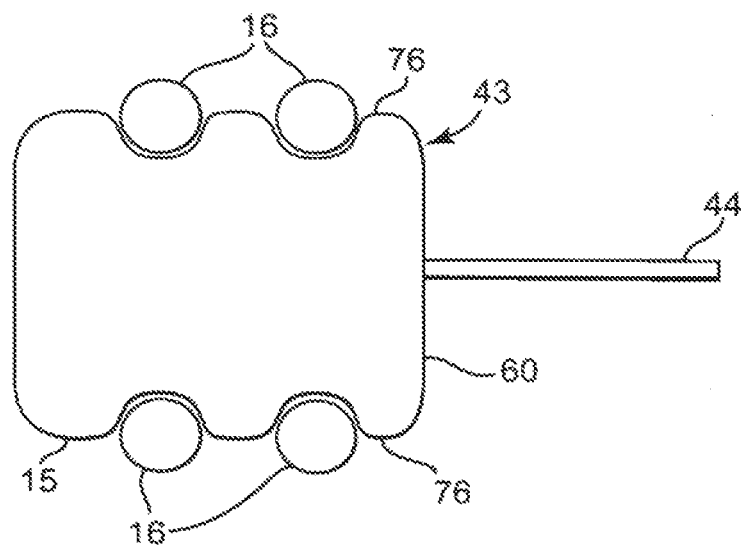
FIG. 15 is a top view of an ablation apparatus according to another embodiment of the invention with an ablator as a contoured patch.

FIGS. 6 and 15 illustrate two embodiments of a contoured patch ablator 43 having a predefined shape with contoured edges 76. The contoured edges 76 can bear against structures In the heart, such as the pulmonary veins 16, to position the tissue engagement surface 60 against the target tissue 15. As shown in FIG. 6, ablating elements 68 can be connected to a power source 46 by the conductor 44 extending through an insertion tool 32 for either epicardial or endocardial use.

Figure 7:
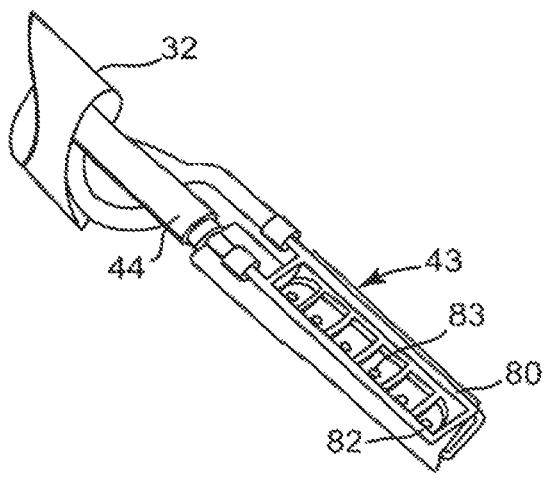
FIG. 7 is a perspective view of an ablation apparatus according to another embodiment of the invention with an ablator as a bipolar electrode.

FIG. 7 illustrates an ablator 43 having two ablating elements, a first ablating element 80 and a second ablating element 82. A conductor 44 may be used to connect the first and second ablating elements 80, 82 together or separately for individual control. In one embodiment, ablating elements 80, 82 may comprise electrodes, which can be energized using radio frequency energy. Ablating elements 80, 82 may be held in contact with tissue by a vacuum applied to ports 83. Alternatively, the first ablating element 80 may be a high intensity focused ultrasound (HIFU) crystal transmitter or transducer and the second ablating element 82 can be another HIFU crystal transmitter or transducer, both of which can focus ultrasound energy on the target tissue 15. Alternatively, the first and second ablating elements 80, 82 may be microwave antennae, which can deliver microwave ablation energy to the target tissue 15. The ablator 43 may be used, in some embodiments, from a location within the esophagus to focus ablation energy on the posterior left atrium of the heart.

Figure 8:
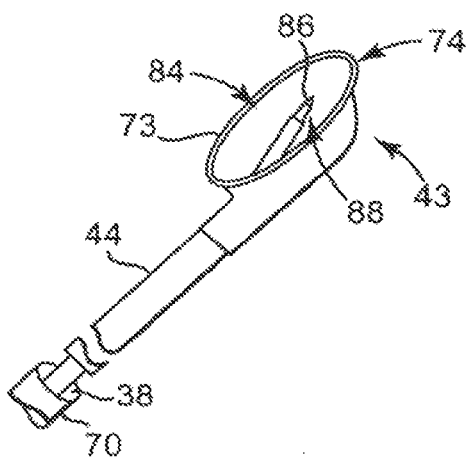
FIG. 8 is a perspective view of an ablation apparatus according to another embodiment of the invention with a suction tent having a wiper.

FIG. 8 illustrates an ablator 43 having a skirt 73 and a deployable wiper 8b that can be placed in the patient to surround the target tissue 15. The skirt 73 can be held to the target tissue 15 by a vacuum applied to a suction chamber 84. The deployable wiper 80 can be connected to a conductor 44 and can move within the skirt 73 of the ablator 43 to rotate to an arc around a pivot point (e.g., a motor 88). The deployable wiper 86 may include one or more ablating elements. The deployable wiper 86 can sweep from side to side and/or can rotate 360 degrees and can apply energy to ablate during ail or during a portion of the rotation. The skirt 73 can be collapsible to be removably inserted in a catheter 70. A resilient outer edge 74 can releasably seal onto the target tissue 15 when the vacuum is applied. An air gap between the skirt 73 and the deployable wiper 86 can protect adjacent tissue from harm by the ablation energy. Also, to aid in guiding the ablations within the skirt 73, a lumen can be provided adjacent to the conductor 44 to allow passage of a fiber optic or endoscopic catheter, which can provide visual confirmation of proper positioning of the skirt 73 and of the selected region for ablation.

Figure 9:
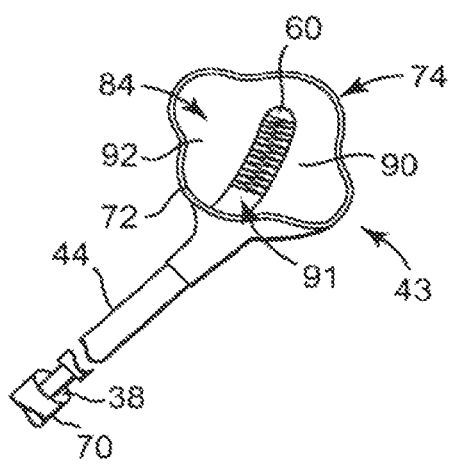
FIG. 9 is a perspective view of an ablation apparatus according to another embodiment of the invention with an ablator as an adhesive tongue electrode.

FIG. 9 illustrates an ablator 43 including an adhesive tongue 90 having a footprint extending from a catheter 70. A skirt 72 can be used to ablate tissue within m outer edge 74. The adhesive tongue 90 can be removably attached to the target tissue 15 for directed ablation by a vacuum applied through a conductor 44. In other embodiments, contact may be facilitated with a biological compatible glue or adhesive 91 on a tissue engagement surface 60. A conductive fluid 92 can be used in a chamber 84 of the skirt 72 to translate the ablating energy to all tissue within the outer edge 74. Alternatively, epicardial application of the adhesive tongue 90 with slow release ablation, chemicals can be used to ablate tissue. The adhesive tongue 90 can also include, in some embodiments, anti-arrhythmia medications or other medications.

Figure 10:
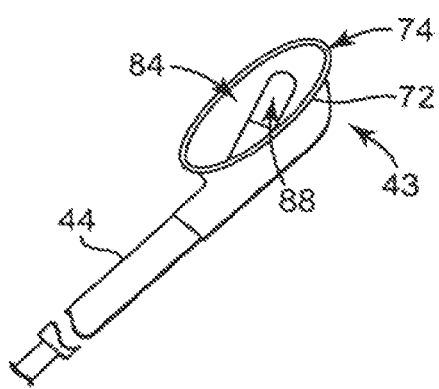
FIG. 10 is a perspective view of an ablation apparatus according to another embodiment of the invention with a head having a cauterizing chemical applicator.

FIG. 10 illustrates as ablator 43 designed to deliver one or more ablation agents, e.g., chemical ablation agents and/or radioactive ablation agents. A conductor or conduit 44 can transfer an ablative agent through a tip 96 to come in contact with tissue within an outer edge 74 of a skirt 72. The tip 96 can be removably Inserted into a catheter 70 to be positioned in the left atrium. The catheter 70 east be manipulated and rotated to cause the skirt 72 to cover the target tissue 15. An ablation agent can be introduced into & chamber 84 within the shirt 72 to ablate the target tissue 15. Following the ablation procedure, any remaining ablation agent may be removed back through tip 96. In some embodiments, tip 96 may be designed for mechanical injection and/or needle-less injection of an ablation agent into tissue. In one embodiment, the ablation agent diffuses into the tissue to be treated. Alternatively, the ablation agent is delivered via controlled slow-release delivery and/or iontophoresis techniques.

Figure 11:
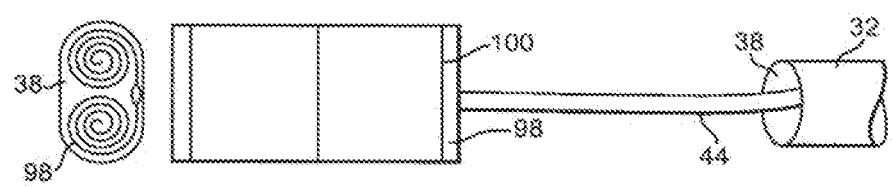
FIG. 11 is a top view and an end view of an ablation apparatus according to another embodiment of the invention with a rolled electrode for insertion in a catheter or other delivery tool.

FIG. 11 illustrates an ablator 43 including a rolled ablating element 98 that can he rolled into a single roll or parallel rolls and can be removably inserted in an insertion tool 32. S-shaped memory wires 100 can unroll the rolled ablating element 98 when a conductor 44 urges the rolled ablating element 98 out of a lumen 38. The rolled ablating element 98 can be rolled for placement between the heart 10 and pericardium for epicardial ablation onto the external surface 14 of the target tissue 15. The rolled ablating element 98 can be similar to the circular and contoured embodiments shown in FIGS. 5 and 6, respectively.

Figure 12:
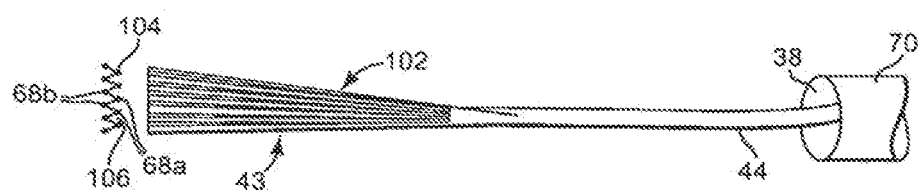
FIG. 12 is a side view of an ablation apparatus according to another embodiment of the invention with a web ablator.

FIG. 12 illustrates an ablator 43 including a webbed tan 102 having ablating elements 68a and 68b positioned in an apex 104 of each fold 106. The ablating elements 68a when positioned adjacent the target tissue 15 can be energized and the ablating elements 68b spaced from the target tissue 15 can remain non-energized to protect tissue outside the area of target tissue 15. The webbed fan 102 can include an insulation layer on one side. The webbed fan 102 can he unfolded into a flat sheet to energize all or a portion of the ablating elements 68a, 68b. The webbed fan 102 may be compressed to be removably inserted in a lumen 38 of a catheter 70.

Figure 13A:
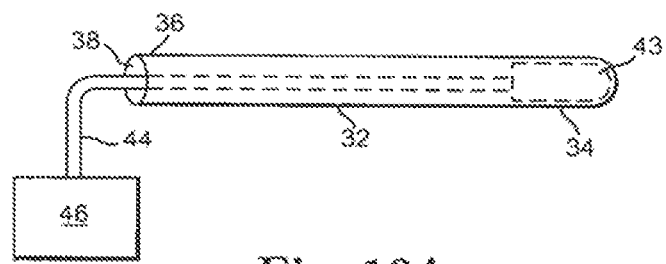
FIGS. 13A and 13B are perspective views of an ablation apparatus according to another embodiment of the invention having an expandable mesh with electrodes.
Figure 13B:
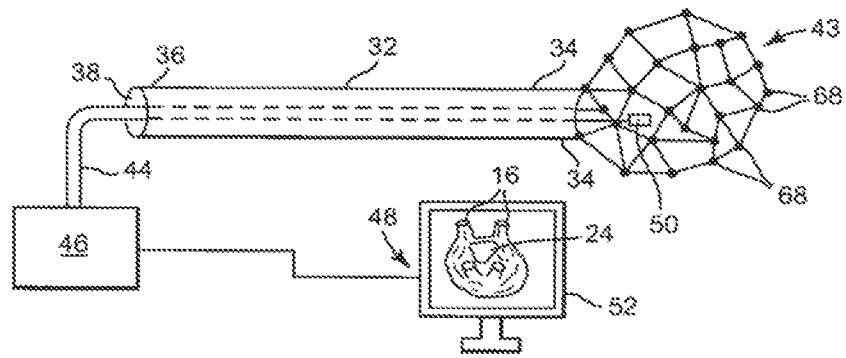

FIGS. 13A and 13B illustrate an ablator 43 with an expandable mesh with numerous ablating elements 68. The ablator 43 can be positioned in the left atrium using an insertion tool 32. Each ablating element 68 can be individually represented using a mapping tool 48 and displayed on a display 52. A conductor 44 can allow individual electrodes 68 in contact with the target tissue 15 to be energized by a power source 46 to ablate tissue. One or more sensors 50 can be positioned inside the expandable mesh to locate the target tissue 15. The ablating elements 68 on the expandable mesh that are contacting the posterior left atrium can be selected. Selection can be facilitated by electrophysiological mapping, computerized complex, algorithms, imaging, individual addressing of smart ablating elements 68, or other suitable methods. The appropriate ablating elements 68 can be are energized either individually or collectively to create an area of ablated tissue on the posterior.

Figure 14:
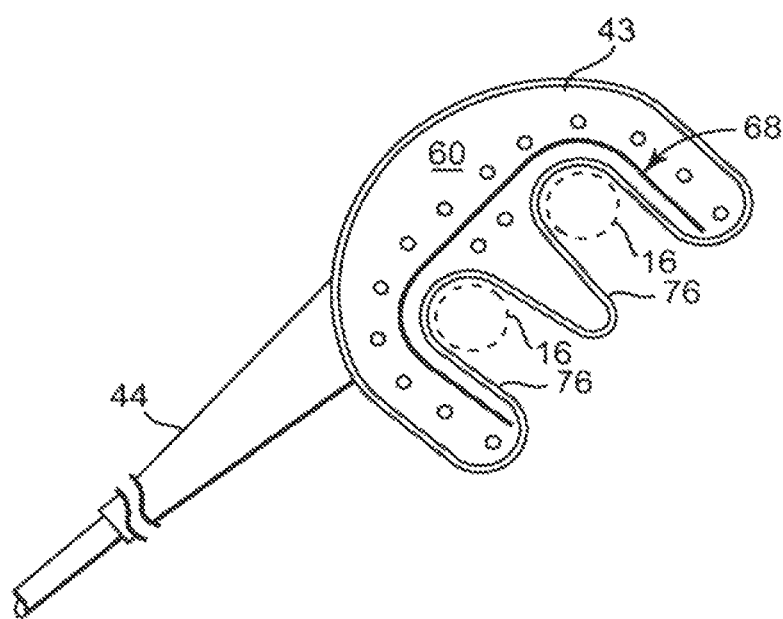
FIG. 14 is a side view of an ablation apparatus according to another embodiment of the invention with a contoured ablator for ablating adjacent to the pulmonary veins.

FIG. 14 illustrates a contoured ablator 43 with a predefined shape defined by contoured edges 76. The contoured edges 76 can bear against structures on the heart, such as the pulmonary veins 16 to position a tissue engagement surface 60 against the target tissue 15. One or more ablating elements 68 can be connected to a power source (not shown) by a conductor 44.

Figure 16:
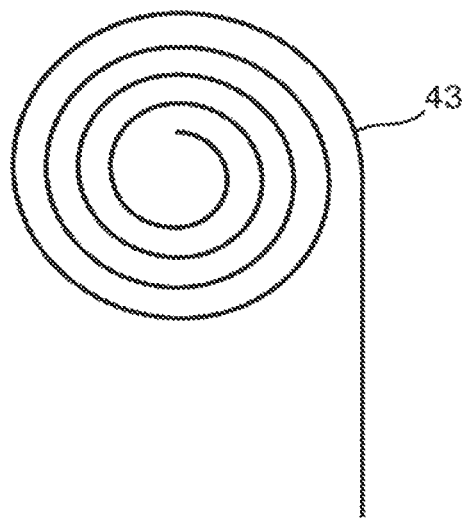
FIG. 16 is a top view of an ablation apparatus according to another embodiment of the invention with a rolled electrode for insertion its a catheter or other delivery tool.

FIG. 16 illustrates a coiled linear ablator 43 with one or more coiled ablating elements that can be deployed out of an Insertion tool 32 (e.g., a sheath) to create an area for ablation. In some embodiments, the coiled linear ablator 43 can deliver energy in one direction (e.g., toward the epicardial surface of the posterior left atrium).

In some embodiments, the ablator 43 (e.g., an ablation energy transmitting member having one or more ablating elements) may be remote from the target tissue 15. For example, ultrasound energy may be focused remotely on the target tissue 15, causing ablation of the target tissue 15, while passing without ablating through non-targeted tissue located between the targeted tissue and ablator 43 The location of the energy focus on the target tissue 15 can be moved throughout the region to be ablated by steering a focal point about a non-linear area to be ablated. A steering mechanism can be manual (e.g., by physically moving an ultrasound transducer relative to the tissue) or electrical (e.g., by using phased arrays of ultrasound transducers or by otherwise modifying the ultrasound focal zone).

Some embodiments of the invention are effective at terminating atrial fibrillation, yet can be performed more safety than some conventional methods. Some embodiments of the invention can perform ablations more quickly than some conventional methods. Some embodiments of the invention can also be used to amputate, ligate, staple, etc. the left atrial appendage (LAA) of the heart—a major source of clots and strokes in the population. Some embodiments of the invention result in less trauma to the patient and less chance of accidentally damaging the heart and surrounding structures. Some embodiments of the invention can minimize the sixe of the incision required to insert the ablation apparatus 30 and/or the ablator 43 through the chest wall. Some embodiments of the invention can eliminate the need for contiguous, linear lesions to treat atrial fibrillation. Some embodiments of the invention can allow the surgeon to create lesions in the heart from the epicardial surface of the beating heart. Some embodiments of the invention can he practiced via transvenous catheters from the inside of the heart.

Various additional features and advantages of the invention are set forth in the following claims.

The invention claimed is:

1. An ablation apparatus for ablating target tissue of a patient, the ablation apparatus comprising:
an insertion tool having a proximal end, a distal end, and a lumen;
an ablator including a conductor and a tissue engagement portion, the conductor having a source end extending from the proximal end of the insertion tool and a delivery end connected to the tissue engagement portion, the ablator removably inserted in the lumen, wherein the tissue engagement portion includes a skirt and the delivery end includes an adhesive tongue inside the skirt, the tongue moveable within the skirt to engage target tissue, and the skirt affixing the ablator to target tissue by a vacuum; and
an energy source connected to the conductor;
the insertion tool configured to be inserted into a patient so that the distal end is adjacent the target tissue;
wherein the ablation apparatus is configured such that:
the conductor is operable to urge the ablator out of the lumen to engage target tissue;
energy conducted from the energy source to the ablator is configured to create a footprint on target tissue to reduce an overall mass of excitable tissue.

2. The ablation apparatus of claim 1 and further comprising a sensor connected to the ablator to sense the target tissue.

3. The ablation apparatus of claim 1 and further comprising a mapping tool to visualize the tissue engagement portion of the ablator.

4. The ablation apparatus of claim 1 wherein the insertion tool includes a catheter.

5. The ablation apparatus of claim 1 the skirt is configured to receive fluid for conducting the energy to the target tissue.

6. The ablation apparatus of claim 5 wherein the fluid is electrically conductive.

7. The ablation apparatus of claim 5 wherein the fluid is caustic.

8. The ablation apparatus of claim 5 wherein the fluid is thermally conductive.

9. The ablation apparatus of claim 1 wherein the ablator includes a chemical delivery system.

10. The ablation apparatus of claim 9 wherein the chemical delivery system is configured to provide at least one of diffusion, iontophoresis, mechanical injection, needle-less injection, and controlled slow-release delivery.

* * * * *